United States Patent
Bratz et al.

[11] Patent Number: 5,981,440
[45] Date of Patent: Nov. 9, 1999

[54] STABLE SOLID FORMULATIONS OF CYCLOHEXENONE OXIME ETHER HERBICIDES

[75] Inventors: Matthias Bratz; Karl-Friedrich Jäger, both of Limburgerhof; Rainer Berghaus, Speyer; Hans Ziegler, Mutterstadt, all of Germany

[73] Assignee: BASF Aktiengesellschaft, Ludwigshafen, Germany

[21] Appl. No.: 08/913,779

[22] PCT Filed: Mar. 12, 1996

[86] PCT No.: PCT/EP96/01046

§ 371 Date: Sep. 23, 1997

§ 102(e) Date: Sep. 23, 1997

[87] PCT Pub. No.: WO96/29869

PCT Pub. Date: Oct. 3, 1996

[30] Foreign Application Priority Data

Mar. 24, 1995 [DE] Germany ............ 195 10 887

[51] Int. Cl.⁶ .......... A01N 43/56; A01N 43/02; A01N 37/00; A01N 35/10
[52] U.S. Cl. .......... 504/344; 504/140; 504/142; 504/344; 504/139
[58] Field of Search .................. 504/129, 118, 504/130, 139, 148, 344, 142, 140

[56] References Cited

U.S. PATENT DOCUMENTS

| | | | |
|---|---|---|---|
| 4,741,768 | 5/1988 | Frazier et al. | 71/98 |
| 4,952,232 | 8/1990 | Cuomo et al. | 71/92 |
| 4,975,113 | 12/1990 | Marrs et al. | 71/121 |
| 5,069,709 | 12/1991 | Bellina | 71/90 |
| 5,084,087 | 1/1992 | Hazen et al. | 71/123 |
| 5,276,188 | 1/1994 | Chalmers et al. | 564/256 |
| 5,341,932 | 8/1994 | Chen et al. | 206/524 |
| 5,354,889 | 10/1994 | Chalmers et al. | 564/256 |

FOREIGN PATENT DOCUMENTS

| | | |
|---|---|---|
| 503917 | 4/1993 | Australia . |
| 394 847 | 10/1990 | European Pat. Off. . |
| 488 645 | 6/1992 | European Pat. Off. . |
| 3941160 | 12/1989 | Germany . |
| 58-144384 | 2/1982 | Japan . |
| 59-163363 | 9/1984 | Japan . |
| 62089654 | 9/1985 | Japan . |

OTHER PUBLICATIONS

Nalewaja et al, Sethoxydim Response to Spray Carrier Chemical Properties and Environment, Weed Technology, vol. 8, pp. 591–7, 1994.
Chem. Abst., vol. 122, No. 1, Abst. No. 3446.
Weed Technology, vol. 7, No. 2, 1993, pp. 322–325.
Chem. Abst., vol. 116, No. 23, Abst. No. 230158.
Database WPI, Section Ch, Week 8216, London, GB.

Primary Examiner—Jose' G. Dees
Assistant Examiner—Alton Pryor
Attorney, Agent, or Firm—Keil & Weinkauf

[57] ABSTRACT

Crop protection active compound formulations, comprising a cyclohexenone oxime ether of the general formula I

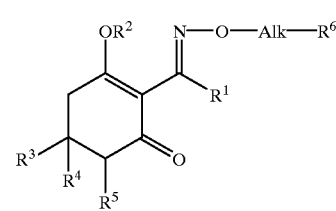

where the radicals $R^1$–$R^6$ have the following meanings:

$R^1$ is ethyl or propyl;

$R^2$ is hydrogen or an equivalent of an agriculturally utilizable cation;

$R^3$ is 2-thioethylpropyl, tetrahydrothiopyran-3-yl, tetrahydrothiopyran-4-yl, tetrahydropyran-3-yl, tetrahydropyran-4-yl, 1-methylthiocyclopropyl, 5-isopropylisoxazol-3-yl, 2,5-dimethylpyrazol-3-yl, 2,4,6-trimethylphenyl or 2,4,6-trimethyl-3-butyrylphenyl;

$R^4$ and $R^5$ independently of one another are hydrogen, methyl or methoxycarbonyl;

Alk is $CH_2CH_2$, $CH_2CH(CH_3)$, $CH_2CH=CH$, $CH_2CH=C(Cl)$ or $CH_2CH_2CH=CH$;

$R^6$ is hydrogen, phenyl, halophenyl, dihalophenyl, phenoxy, halophenoxy or dihalophenoxy;

and a water-soluble basic salt of an acid having a $pK_a$ of greater than 5, alkali metal hydroxides and alkali metal carbonates being excluded, their preparation and use as herbicides are described.

16 Claims, No Drawings

STABLE SOLID FORMULATIONS OF CYCLOHEXENONE OXIME ETHER HERBICIDES

This application is a 371 of pct/EP96/01046 filed Mar. 3, 1996.

The present invention relates to crop protection active compound formulations, comprising a cyclohexenone oxime ether of the general formula I

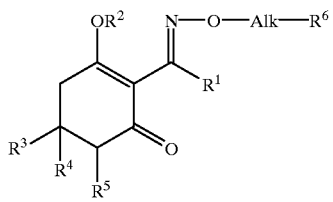

where the radicals $R^1$–$R^6$ have the following meanings:

$R^1$ is ethyl or propyl;

$R^2$ is hydrogen or an equivalent of an agriculturally utilizable cation;

$R^3$ is 2-thioethylpropyl, tetrahydrothiopyran-3-yl, tetrahydrothiopyran-4-yl, tetrahydropyran-3-yl, tetrahydropyran-4-yl, 1-methylthiocyclopropyl, 5-isopropylisoxazol-3-yl, 2,5-dimethylpyrazol-3-yl, 2,4,6-trimethylphenyl or 2,4,6-trimethyl-3-butyrylphenyl;

$R^4$ and $R^5$ independently of one another are hydrogen, methyl or methoxycarbonyl;

Alk is $CH_2CH_2$, $CH_2CH(CH_3)$, $CH_2CH=CH$, $CH_2CH=C(Cl)$ or $CH_2CH_2CH=CH$;

$R^6$ is hydrogen, phenyl, halophenyl, dihalophenyl, phenoxy, halophenoxy or dihalophenoxy;

and a water-soluble basic salt of an acid having a $pK_a$ of greater than 5, and their preparation and use as herbicides.

Cyclohexenone oxime ethers of the general formula I have been known as herbicides for a long time. Moreover, in small amounts they act as growth regulators.

The herbicidally active cyclohexenone oxime ethers of the general formula I are disclosed, inter alia, in DE-A 24 39 104, DE-A 28 22 304, DE-A 38 08 072, DE-A 38 38 309, EP-A 046 860, EP-A 066 195, EP-A 071 707, EP-A 088 299, EP-A 088 301, EP-A 115 808, EP-A 125 094, EP-A 137 174, EP-A 142 741, EP-A 177 913, EP-A 228 598, EP-A 230 235, EP-A 230 260, EP-A 238 021, EP-A 243 313, EP-A 254 514, EP-A 319 835, EP-A 456 068, EP-A 456 069, EP-A 456 112, EP-A 456 118, U.S. Pat. No. 4,440,566, JP-A 54/191 945 and Proceedings Brit. Crop Protection Conference—Weeds 1985, Vol. 1, pages 93–98.

Metal salts of cyclohexenone oxime ethers are also disclosed, inter alia, in the earlier German Patent Application having the file reference 195 45 212.7.

These compounds are in general used in the form of water-dispersible powders (WP) or water-dispersible granules (WG), and also as emulsifiable concentrates (EC). Some compounds of this class of substances are marketed as water-soluble formulations in which the active compound is present as the alkali metal salt. A disadvantage of the emulsifiable concentrates is that, beside the actual active compound, large amounts of organic solvents are also applied during use. It has additionally been shown that the active compounds are unstable in organic solvents in the presence of emulsifiers or of water present in traces and decompose (cf., for example, EP-A 394 847 and EP-A 266 068).

Water-dispersible solid formulations (WP or WG) do avoid the use of organic solvents, but require a higher expenditure on preparation of the formulation. The often low-melting or liquid active compounds must be absorbed on carrier material in order to be accessible to the necessary fine grinding. The addition of auxiliaries and carriers additionally leads to the fact that the active compound contents in the formulations have to precipitate to a low extent, which leads to increased packaging and transportation costs. Examples of such formulations are found, inter alia, in EP-A 488 645.

Water-soluble formulations have also been described previously. It is also seen here that the chemical instability of the cyclohexenone oxime ethers stands in the way of a practical solution. A lithium salt, for example, is thus described in JP 62089 635.

The preparation of various salts, among these salts of transition metals, by double decomposition is described in various applications. In practice, this process appears unsuitable as in the end sufficient stability is not achieved. (JP 59 1633 63, JP 8144 384, U.S. Pat. No. 4,741,768, DE 3941160).

The preferred manner of preparation of alkali metal salts is the extraction of the active compounds from organic solution using an aqueous solution of the alkali metal hydroxides (eg. DE 3941160).

It is an object of the present invention to develop storage-stable solid formulations of cyclohexenone oxime ethers of the general formula I and a process for their preparation.

We have found that this object is surprisingly achieved by the crop protection active compound formulation described at the out-set.

Within the meaning of the present invention, the cyclohexenone oxime ethers are weak organic acids having $pK_a$s between 4 and 5. Their low solubility in water in the neutral range distinctly increases at basic pHs. It is thus possible by suitable combination of cyclohexenones with basic water-soluble substances (acid acceptors) to obtain water-soluble mixtures.

Beside the alkali metal hydroxides and alkali metal carbonates mentioned in the literature, basic water-soluble substances which are suitable for this purpose are those which are to be interpreted as alkali metal salts of those acids whose $pK_a$ is greater than 5. The $pK_a$ of the particular cyclohexenone is preferably checked and then a basic substance is selected whose underlying $pK_a$ is greater than that of the cyclohexenone in question.

It is to be expected that the following reaction commences in the presence of water:

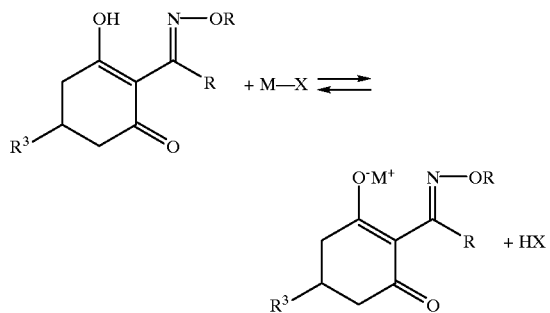

A requirement for a clear solution then being formed is also that the conjugate acid HX formed is also water-soluble.

Beside water-solubility, the formulations of cyclohexenone and water-soluble basic salt (acid acceptor) according to the invention have a distinctly improved storage stability at elevated temperatures than, for example, the free active compounds or their alkali metal salts which were obtained from the cyclohexenones with alkali metal hydroxides or alkali metal carbonates.

Adequate storage stability is an essential feature of commercially marketable and registrable crop protection agents. Decreased decomposition of the active compound per se is also an economic advantage.

Suitable water-soluble basic salts for achieving the described water solubility and storage stability of the active compound are: metaborates, phosphates, hydrogen phosphates, pyrophosphates, metasilicates, orthosilicates, tetraborates, sulfites, tripolyphosphates, polyphosphates, metaphosphates, citrates, tetrasodium EDTA, trisodium nitrilotriacetate, guanidine acetate, guanidine carbonate, and mixtures of these.

The following basic water-soluble salts are preferred: ammonium and alkali metal metaborates, tetraborates, metasilicates, orthosilicates, phosphates, hydrogen phosphates, pyrophosphates, tripolyphosphates, polyphosphates, sulfites, citrates, tetrasodium EDTA, trisodium nitrilotriacetic acid, guanidine carbonate and guanidine acetate. The salts can be employed in anhydrous form and in the form of their hydrates.

Alkali metal metaborates, alkali metal tetraborates, alkali metal and ammonium metasilicates, trialkali metal and triammonium phosphates, alkali metal and ammonium hydrogen phosphates, alkali metal pyrophosphates, alkali metal tripolyphosphates, alkali metal sulfites, alkali metal citrates, tetrasodium EDTA, trisodium nitrilotriacetic acid, guanidine carbonate and guanidine acetate are particularly preferred, it being possible for the salts to be present in anhydrous form or as hydrates.

The sodium and potassium salts are preferred.

Tetrasodium pyrophosphate, dipotassium hydrogen phosphate, guanidine carbonate, tetrasodium EDTA, trisodium nitrilotriacetic acid and especially sodium metaborate, sodium metasilicate and trisodium phosphate have proven to be very particularly suitable from which, in turn, sodium metasilicate particularly stands out.

Preferred cyclohexenone herbicides are:

2-(N-ethoxybutyrimidoyl)-5-(2-ethylthiopropyl)-3-hydroxy-2-cyclohexen-1-one (sethoxydim), 2-(1-allyloxyiminobutyl)-4-methoxycarbonyl-5,5-dimethyl-3-oxocyclohexenol (alloxydim), 2-(N-ethoxybutyrimidoyl)-5-(2-phenylthiopropyl)-3-hydroxy-2-cyclohexen-1-one, 5-(2,4,6-trimethylphenyl)-3-hydroxy-2-[1-(ethoxyimimo)propyl]-cyclohex-2-en-1-one (tralkoxydim), 2-(N-ethoxybutyrimidoyl)-3-hydroxy-5-(tetrahydropyran-3-yl)cyclo-hexen-1-one, 1-[1-ethoxyiminobutyl]-3-hydroxy-5-(tetrahydrothiopyran-3-yl)-2-cyclohexen-1-one (cycloxydim), 2-[1-[(E)-3-chloroallyloxy]iminopropyl]-5-(2-ethylthiopropyl)-3-hydroxycyclohex-2-enone (clethodim), 2-(1-(3-chloroallyloxyiminobutyl)-5-(2-ethylthio)propyl)-3-hydroxycyclohex-2-enone (cloproxydim), 2-(1-(3-chloroallyloxy)iminopropyl)-5-(1,3-dimethylpyrazol-5-yl)-3-hydroxycyclohex-2-enone, 2-(1-(3-chloroallyloxy)iminopropyl)-5-(1-thiomethylcyclopropyl)-3-hydroxycyclohex-2-enone, 2-(1-ethoxyiminopropyl)-5-(2,4,6-trimethyl-3-butyrylphenyl)-3-hydroxycyclohex-2-enone (butroxydim), 2-(1-(3-chloroallyloxy)iminopropyl)-5-(tetrahydropyran-4-yl)-3-hydroxycyclohex-2-enone, 2-(1-(2-p-chlorophenoxypropyloxy)iminobutyl-5-(tetrahydrothio-pyran-3-yl)-3-hydroxycyclohex-2-enone or mixtures thereof.

Particularly preferred cyclohexenone herbicides are:

sethoxydim, cycloxydim, clethodim, tralkoxydim, butroxydim, 2-(1-(3-chloroallyloxy)iminopropyl)-5-(tetrahydropyran-4-yl)-3-hydroxycyclohex-2-enone, 2-(1-(2-p-chlorophenoxypropyloxy)-iminobutyl-5-(tetrahydrothiopyran-3-yl)-3-hydroxy-cyclohex-2-en-one or mixtures thereof.

The cyclohexenone oxime ethers of the general formula I can be obtained during preparation as isomer mixtures, both E/Z isomer mixtures and enantiomer or diastereoisomer mixtures being possible. If desirable, the isomer mixtures can be separated by the methods customary for this purpose, eg. by chromatography or by crystallization.

The cyclohexenone oxime ethers of the general formula I can be present in several tautomeric forms, which are all covered by the invention.

The invention comprises solid water-soluble formulations, preferably in the form of powders or granules, which as the herbicidal component comprise a cyclohexenone oxime ether and a water-soluble basic salt. The proportion of the cyclohexenone oxime ether is from 5 to 95%, preferably from 10 to 85%, and the proportion of the basic salt is from 5 to 95%, preferably from 15 to 90%, based on the sum of cyclohexenone oxime ether and basic salt.

In order to guarantee use in accordance with practice, it may be necessary to add further formulation auxiliaries. These include, for example, herbicidally active compounds, antidotes, water-soluble salts, dispersants, wetting agents, binders, lubricants, absorptive carriers, antifoams, preservatives, colorants, pigments or further adjuvants or surfactants customary in agricultural practice.

Additional water-soluble salts can be: sodium chloride, potassium chloride, ammonium sulfate, sodium sulfate, potassium sulfate, potassium carbonate and sodium carbonate.

Further herbicidally active compounds can be:

2,4-D, 2,4-DB, acetochlor, acifluorfen, aclonifen, alachlor, allidochlor, ametryn, amidosulfuron, amitrole, anilofos, asulam, atrazine, azimsulfuron, aziprotryne, barban, benazolin, benfluralin, benfuresate, bensulfuron, bensulide, bentazone, benzofenap, benzofluor, benzoylprop, benzthiazuron, bifenox, bisalafos, bromacil, bromobutide, bromofenoxim, bromoxynil, buminafos, butachlor, butamifos, butenachlor, buthidazole, butralin, buturon, butylate, cafenstrole, carbetamide, chloramben, chlorbromuron, chlorbufam, chlorfenac, chloridazon, chlorimuron, chlornitrofen, chlorfenprop, chloroxuron, chlorpropham, chlorsulfuron, chlorthal-dimethyl, chlorthiamid, chlortoluron, cinmethylin, cinosulfuron, clodinafop, clomazone, clomeprop, clopyralid, cumyluron, cyanazine, cycloate, cyclosulfamuron, cycluron, cyhalofop, cyperquat, cyprazine, cyprazole, dalapon, desmedipham, desmetryn, di-allate, dicamba, dichlobenil, dichlorprop, dichlorprop-P, diclofop, diethatyl, difenoxuron, difenzoquat, diflufenican, dimefuron, dimethachlor, dimethametryn, dimethenamid, dinitramine, dinoseb, dinoterb, diphenamid, dipropetryn, diquat, dithiopyr, diuron, DNOC, dymron, eglinazine, endothal, EPTC, esprocarb, ethalfluralin, ethametsulfuron, ethidimuron, ethiozin, ethofumesate, ethoxyfen, etobenzanid, fenoprop, fenoxaprop, fenoxaprop-P, fenthiaprop, fenuron, flamprop, flazasulfuron, fluazifop, fluazifop-P, fluchloralin, flumetsulam, flumiclorac, flumioxazin, flumipropyn, fluometuron, fluorbentranil, fluorochloridone, fluorodifen, fluoroglycofen, flupoxam, flupropacil, fluridone, fluroxypyr, flurtamone, fomesafen, fosamine, furyloxyfen, glufosinate-ammonium, glyphosate, halosulfuron, haloxyfop, haloxyfop-P, hexazinone, imazamethapyr, imazapyr, imazaquin, imazethabenz, imazethapyr, imazosulfuron, ioxynil, isocarbamid, isopropalin, isoproturon, isouron, isoxaben, isoxapyrifop, karbutilate, lactofen, lenacil, linuron, maleic hydrazide, MCPA, MCPB, mecoprop, mecoprop-P, mefenacet, mefluidide, metamitron, metazachlor, methabenzthiazuron, methazole, metobenzuron, metolachlor, metosulam, metoxuron, metribuzin, metsulfuron, minoterb, molinate, monalide, monolinuron, monuron, napropamide, naproanilide, naptalam, NCC 330, neburon, nicosulfuron, nipyraclofen, nitralin, nitrofen, nitrofluorfen, norflurazon, orbencarb, oryzalin, oxadiargyl, oxadiazon, oxyfluorfen, paraquat, pebulate, pendimethalin, perfluidone, phenisopham, phenmedipham, picloram, piperophos, PPG-1013, pretilachlor, primisulfuron, procyazine, prodiamine, profluralin, prometon, prometryn, propyzamide, propachlor, propanil, propaquizafop, propazine, propham, prosulfocarb, prosulfuron, prynachlor, pyrazolate, pyrazosulfuron, pyrazoxyfen, pyributicarb, pyridate, pyrithiobac, quinclorac, quinmerac, quizalofop, quizalofop-P, rimsulfuron, secbumeton, siduron, simazine, simetryn, sulcotrione, sulfallate, sulfentrazone, sulfometuron-methyl, sulfosate, tebuthiuron, terbacil, terbucarb, terbuchlor, terbumeton, terbuthylazine, terbutryn, thiazopyr, thidiazimin, thifensulfuron-methyl, thiobencarb, tiocarbazil, triallate, triasulfuron, triazofenamid, tribenuron, triclopyr, tridiphane, trietazine, trifluralin, triflusulfuron, trimeturon, vernolate, xylachlor or mixtures of these. The co-herbicides can be water-soluble or water-insoluble.

In the case of water-insoluble compounds, these are present as finely ground powders. It is additionally possible to introduce these into the formulation in the form of water-dispersible granules. In the case of water-soluble co-herbicides, these can be present in the form of the free acid or as its salt.

Dispersants or wetting agents which can be used, inter alia, are: alkylarylsulfonates; phenylsulfonates; alkylsulfates; alkylsulfonates; alkyl ether sulfates; alkyl aryl ether sulfates; alkyl polyglycol ether phosphates; polyarylphenyl ether phosphates; alkylsulfosuccinates; olefinsulfonates; paraffinsulfonates; petroleumsulfonates; taurides; sarcosides; fatty acids; alkylnaphthalenesulfonic acids; naphthalenesulfonic acids; lignosulfonic acids; condensation products of sulfonated naphthalenes with formaldehyde; or with formaldehyde and phenol; ligninsulfite waste liquor; including their alkali metal, alkaline earth metal, ammonium and amine salts; alkylphenol alkoxylates; alcohol alkoxylates; fatty amine alkoxylates; polyoxyethylene glycerol fatty acid esters; castor oil alkoxylates; fatty acid alkoxylates; fatty acid amide alkoxylates; fatty acid polydiethanolamides; lanolin ethoxylates; EO/PO block copolymers; fatty acid polyglycol esters; isotridecyl alcohol; fatty acid amides; methylcellulose; fatty acid esters; silicone oils; alkyl polyglycosides; glycerol fatty acid esters; alkyl phosphates; quaternary ammonium compounds, amine oxides; betaines and mixtures of these. The dispersants and wetting agents are known substances and are described in greater detail, for example, in: McCutcheons: Emulsifiers & Detergents, MC Division, Glen Rock N.J.; Stache, Tensid Taschenbuch [Surfactant Handbook], Hanser Verlag.

Binders which can be used are:
polyvinylpyrrolidone, polyvinyl alcohol, carboxymethylcellulose, starch, vinylpyrrolidone/vinyl acetate copolymers and mixtures thereof.

Lubricants which can be used are: Mg stearate, Na stearate, talc, polyethylene glycol and mixtures thereof.

Absorptive carrier materials which can be used are: mineral earths such as silicic acids, silica gels, silicates, talc, kaolin, attaclay, limestone, chalk, bole, loess, clay, dolomite, diatomaceous earth, calcium sulfate and magnesium sulfate, magnesium oxide, ground synthetic materials, fertilizers such as ammonium sulfate, ammonium phosphate, ammonium nitrate and ureas, vegetable products such as grain flour, tree bark meal, wood meal and nutshell meal, cellulose powder, attapulgite, montmorillonite, mica, vermiculite, synthetic silicic acids, synthetic calcium silcates and mixtures thereof.

Suitable antifoams are, for example, silicone emulsions, long-chain alcohols, fatty acids, organofluorine compounds and mixtures thereof.

The formulation auxiliaries can be additionally used in the crop protection active compound formulation in a concentration from 0 to 95% by weight. If they are a constituent of the formulation, from 5 to 95% by weight have proven suitable.

Further crop protection active compounds can be additionally used in a concentration from 0 to 90% by weight. If they are a constituent of the formulation, from 10 to 90% by weight have proven suitable. The % by weight mentioned relate to the total weight of the crop protection active compound formulation.

The solid formulations according to the invention can be prepared in various manners known in principle to the person skilled in the art.

Suitable formulations are powders, granules, briquets, tablets and similar solid formulations. In addition to powders, granules are particularly preferred. The powders can be water-soluble or water-dispersible powders. The granules can be water-soluble or water-dispersible granules for use in spray application or broad-casting granules for direct application. The average particle size of the granules is from 200 $\mu$m to 2 mm.

Since these formulations are often hygroscopic substances, or for the purpose of preventive user protection, for instance, the formulations can be packaged in water-soluble film bags. Preferably, a water vapor-impermeable outer covering such as polyethylene film, polyethylene-laminated paper or aluminum foil is additionally employed in the packaging.

Suitable water-soluble films consist of the following materials:
polyvinyl alcohol, cellulose derivatives such as methylcellulose or carboxymethylcellulose.

Undesired vegetation is controlled by allowing a herbicidally active amount of a crop protection active compound formulation to act on the crop plant, its habitat and/or on its seed.

The following preparation processes are suitable for the formulations according to the invention:

a) Active Compound is Solid

1) Mixing of active compound, basic salt and further auxiliaries, commutation if desired and subsequent agglomeration.

The processes of extruder granulation, disk granulation, fluidized bed granulation or mixer granulation, for example, are suitable for agglomeration. If appropriate, the granules obtained are then dried.

2) Mixing of active compound, basic salt and further auxiliaries, commutation if desired and subsequent compaction.

b) Active Compound is an Oil or a Solid
  1) Extraction of the cyclohexenone oxime ether dissolved in an organic solvent by means of an aqueous solution of the basic salt in the aqueous phase and subsequent removal of the water.

Suitable organic solvents are water-immiscible, or only partially miscible, solvents such as hydrocarbons, aromatic hydrocarbons, halogenated aliphatic or aromatic hydrocarbons, ethers, carboxylic acid esters, carboxamides, ketones and alcohols.

Spray drying, vacuum drying, fluidized bed drying and freeze drying, for example, are suitable for evaporating the water.

The solids obtained in this way can then be additionally processed as under a).

The aqueous solution thus obtained can furthermore be applied to an absorptive carrier material, e. g. by spraying or mixing. Broadcasting granules, for example, can be obtained in this manner.

FORMULATION EXAMPLES a) Test Methods

The active compound content of the formulations was in each case determined by means of quantitative HPLC, and is indicated in percent.

Experiments on shelf life

To investigate the shelf life, samples of the particular formulation were stored for a specific time at the particular temperature indicated in tightly closed glass vessels. The samples were then examined and compared with the comparison value at the start of storage (zero value). The active compound content is indicated as the relative proportion, based on the zero value (in percent).

Experiments on dissolution behavior 2 g of the formulation were added in one portion to 100 ml of CIPAC standard water D which was stirred at about 100 rpm by means of a magnetic stirrer. The time which passed until the entire solid product had disintegrated or dissolved was taken.

b) Formulation Experiments

The following compounds were used for formulation experiments:

Compound A: sethoxydim

Compound B: cycloxydim

Compound C: 2-(1-(3-chioroallyloxy)imino-propyl)-5-(tetrahydropyran-4-yl)-3-hydroxycyclohex-2-enone Compound D: 2-(1-(2-p-chlorophenoxypropyloxy)imino-butyl-5-(tetrahydrothiopyran-3-yl)-3-hydroxycyclohexenone

Comparison Example 1

51.4 g of compound C (content 97%) were mixed with a mixture of 1 part of sodium carbonate and 1 part of sodium hydrogen carbonate (48.6 g) for 60 sec in an IKA laboratory mill (type M 20). The mixture was soluble in water within less than 5 min. The active compound content was 49.3%.

Example 1

51.4 g of compound C (content 97%) were mixed with sodium metasilicate (48.6 g) for 60 sec in an IKA laboratory mill (type M 20). The mixture was soluble to give a clear solution in water within less than 5 min. The active compound content was 42%.

Example 2

51.4 g of compound C and 48.6 g of trisodium phosphate dodecahydrate were mixed as described in Ex. 1. Active compound content: 46%.

The storage stability at room temperature was observed for 3 months and compared.

|  | Relative content of compound C after | |
|---|---|---|
|  | 1 month [%] | 3 months [%] |
| Comparison Example 1 | 91 | 68 |
| Example 1 | 100 | 95 |
| Example 2 | 99 | 78 |

Comparison Example 2

500 g of active compound C were dissolved in 1,000 g of toluene. This solution was mixed with a solution of 58.5 g of sodium hydroxide in 650 g of water for 1 hour. After phase separation, the homogeneous aqueous phase was separated off and then dried to give granules in a laboratory fluidized bed granulator at an inlet temperature of the drying air of 120° C. The active compound content was 86.8%. The granules dissolved rapidly and completely on introducing into water.

Comparison Example 3

92.3 g of active compound D were dissolved in 90 g of toluene. This solution was mixed with a solution of 7.66 g of sodium hydroxide solution in 100 g of water for 1 hour. After phase separation, the homogeneous aqueous phase was separated off, washed with MTB ether and then dried to give a solid product in a vacuum drying oven at a drying temperature of 40° C. The solid product had an active compound content of 87.1% and dissolved rapidly and completely on introducing into water.

Comparison Example 4

A 30% strength solution of active compound D in toluene was extracted with 2.5% strength NaOH. The aqueous phases were collected and dried at 70° C. in a vacuum drying oven. The solid obtained had an active compound content of 84.6% and was soluble in water to give a clear solution within 2 min.

Example 3

50 ml of a 50% strength solution of compound A in tert-butyl methyl ether were shaken with a solution of 10.2 g of sodium 35 metasilicate in 50 ml of water. After separating off the aqueous phase, the ether phase was washed with 30 ml of water. The combined aqueous phases were evaporated in vacuo at 70° C. The solid residue obtained was soluble to give a clear solution in water within 2 min. Active compound content: 70%.

Example 4

50 ml of a solution of cycloxydim (compound B) in Solvesso 150 (430 g/l) were extracted with a solution of 17.7 g of sodium metasilicate in 85 ml of water. After separating off the aqueous phase, the organic phase was washed with 30 ml of water and the combined aqueous phases were evaporated in vacuo at 70° C. The residue obtained was soluble in water to give a clear solution within 2 min. Active compound content: 57%.

Example 5

A mixture of sodium metaborate hydrate (48.6 g) and compound C (51.4 g) was first mixed in an IKA universal mill, type M 20, and then treated successively with 7.2 ml of water. The material thus obtained was extruded using a basket extruder bench apparatus (Fitzpatrick Company Europe, type KAR 75) with a screen size of 0.8 mm. The granules obtained were dried at 60° C. Active compound content: 55%. The granules dissolved completely in water in less than 4 min.

Example 6

A mixture of sodium phosphate dodecahydrate (58.9 g) and compound C (41.1 g) was extruded as described in Example 5 with addition of 3.8 ml of water. Active compound content: 52%. The granules dissolved in water to give a clear solution within 3 min.

Example 7

A mixture of sodium metasilicate (48.6 g) and compound C (51.4 g) was extruded as described in Example 5 with addition of 25 g of water. Active compound content: 45%. The granules dissolved in water to give a clear solution within 2 min.

Example 8

A mixture of compound C (72%) and sodium metasilicate (28%) was mixed in an IKA type M 20 universal mill and made into a paste with addition of a total of 22.5 g of water. The material obtained was extruded as described in Example 5 and the granules obtained were dried at 60° C. Active compound content: 64%. The granules dissolved in water to give a clear solution within 2 min.

Example 9

217.5 g of active compound C were dissolved in 200 g of toluene. This solution was mixed with a solution of 82.5 g of sodium metasilicate in 300 g of water for 1 hour. After phase separation in a separating funnel, the homogeneous aqueous phase was separated off and then dried to give granules in a laboratory fluidized bed granulator (Combi Coater, Niro Aeromatic) at an inlet temperature of the drying air of 120° C.

The active compound content was 64.2%. The granules dissolved rapidly and completely on introducing into water.

Example 10

16.0g of sodium metasilicate and 84.82 g of active compound C were mixed and reacted in 100 g of water. An aqueous solution was formed. This was dried in a vacuum drying oven at a drying temperature of 70° C. to give a solid product. The active compound content was 73.7%. The solid product dissolved rapidly and completely on introducing into water.

Example 11

79.8 g of active compound D were dissolved in 100 g of toluene. This solution was mixed and reacted with a solution of 20.8 g of sodium metasilicate in 100 g of water for 1 hour. After allowing to stand, 3 phases were formed. The two lower, aqueous phases were separated off in a separating funnel and then dried at a drying temperature of 70° C. in a vacuum drying oven to give a solid product having an active compound content of 78.7%. The solid product dissolved rapidly and completely on introducing into water.

Example 12

88.75 g of active compound D were dissolved in 100 g of toluene. This solution was mixed and reacted with a solution of 11.6 g of sodium metasilicate in 100 g of water for 1 hour. After allowing to stand, 3 phases were formed. The two lower, aqueous phases were separated off in a separating funnel and then dried at a drying temperature of 70° C. in a vacuum drying oven to give a solid product having an active compound content of 88.4%. The solid product dissolved rapidly and completely on introducing into water.

Example 13

Compound C (7.6 g) and bentazone sodium salt (84.7 g; content about 85%) were intimately mixed together with sodium metasilicate (7.7 g) in an IKA universal mill and then moistened with 8.5 ml of water. After extrusion of the material obtained, granules which were soluble in water to give a clear solution within 1 min were obtained. Active compound content (compound C): 45 6.8%.

Example 14

84.7 g of Na bentazone, 7.6 g of compound C, 7.7 g of sodium metaborate and 6 ml of water were mixed and extruded as described in Example 13. The granules obtained were soluble in water to give a clear solution within 1 min. Active compound content (compound C): 6.5%.

Table: Results of the experiments on shelf life of active compounds in formulations at specific temperatures and at a storage time of 30 days. The relative active compound content (%) based on the initial content is indicated.

|  | 20° C. | 30° C. | 40° C. | 50° C. |
| --- | --- | --- | --- | --- |
| Comparison Example No. |  |  |  |  |
| 2 | 100 | 99 | 88 | 42 |
| 3 | 100 | 98 | 88 | 40 |
| 4 | 100 | 96 | 80 | 19 |
| Example No. |  |  |  |  |
| 4 | 100 | 100 | 96 | 96 |
| 5 | 100 | 100 | 98 | 83 |
| 6 | 100 | 99 | 99 | 87 |
| 7 | 100 | 100 | 100 | 99 |
| 8 | 100 | 100 | 100 | 100 |
| 9 | 100 | 100 | 100 | 78 |
| 10 | 100 | 100 | 99 | 77 |
| 11 | 99 | 99 | 99 | 85 |
| 12 | 99 | 99 | 99 | 90 |

We claim:
1. A stable, water-soluble crop protection solid active compound formulation, comprising a cyclohexenone oxime ether of the general formula I

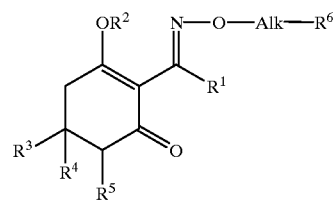

where the radicals $R^1$–$R^6$ have the following meanings:
$R^1$ is ethyl or propyl;
$R^2$ is hydrogen or an equivalent of an agriculturally utilizable cation;
$R^3$ is 2-thioethylpropyl, tetrahydrothiopyran-3-yl, tetrahydrothiopyran-4-yl, tetrahydropyran-3-yl, tetrahydropyran-4-yl, 1-methylthiocyclopropyl, 5-isopropylisoxa-zol-3-yl, 2,5-dimethylpyrazol-3-yl, 2,4,6-trimethylphenyl or 2,4,6-trimethyl-3-butyrylphenyl;

$R^4$ and $R^5$ independently of one another are hydrogen, methyl or methoxycarbonyl;

Alk is $CH_2CH_2$, $CH_2CH(CH_3)$, $CH_2CH=CH$, $CH_2CH=C(Cl)$ or $CH_2CH_2CH=CH$;

$R^6$ is hydrogen, phenyl, halophenyl, dihalophenyl, phenoxy, halophenoxy or dihalophenoxy;

and a water-soluble basic salt of an acid having a $pK_a$ of greater than 5, alkali metal hydroxides, alkali metal carbonates and where: a said formulation excludes ammonium salts.

2. A stable, water-soluble crop protection solid active compound formulation as claimed in claim 1, comprising, as crop protection active compound, a cyclohexenone oxime ether from the group consisting of sethoxydim, cycloxydim, clethodim, tralkoxydim, butroxydim, 2-(1-(3-chloroallyloxy)iminopro-pyl)-5-(tetrahydropyran-4-yl)-3-hydroxycyclohex-2-enone, 2-(1-(2-p-chlorophenoxypropyloxy)-iminobutyl-5-(tetrahydrothiopyran-3-yl)-3-hydroxycyclohex-2-enone or mixtures thereof.

3. A stable, water-soluble crop protection solid active compound formulation as claimed in claim 1, comprising as water-soluble salt a metaborate, phosphate, hydrogen phosphate, pyrophosphate, metasilicate, orthosilicate, tetraborate, sulfite, tripolyphosphate, polyphosphate, metaphosphate, tetrasodium EDTA, trisodium nitrilotriacetate, guanidine acetate, guanidine carbonate or mixtures thereof.

4. A stable, water-soluble crop protection solid active compound formulation as claimed in claim 1, comprising as water-soluble basic salt an alkali metal metaborate, alkali metal tetraborate, alkali metal metasilicate, trialkali metal phosphate, alkali metal hydrogen phosphate, alkali metal pyrophosphate, alkali metal tripolyphosphate, alkali metal sulfite, alkali metal polyphosphate, tetrasodium EDTA, trisodium nitrilotriacetate, guanidine carbonate, guanidine acetate or mixtures thereof.

5. A stable, water-soluble crop protection solid active compound formulation as claimed in claim 1, furthermore comprising formulation auxiliaries.

6. A stable, water-soluble crop protection solid active compound formulation as claimed in claim 1, comprising further crop protection active compounds.

7. A stable, water-soluble crop protection solid active compound formulation as claimed in claim 1, comprising from 5 to 95% by weight of a cyclohexenone oxime ether of the general formula I, from 5 to 95% by weight of a water-soluble basic salt, from 0 to 95% by weight of a formulation auxiliary, from 0 to 90% by weight of further crop protection active compounds.

8. A process for preparing a crop protection solid active compound formulation as claimed in claim 1, which comprises mixing a cyclohexenone oxime ether of the general formula I, the water-soluble basic salt, formulation auxiliaries and optionally further crop protection active compounds, optionally comminuting and then agglomerating or compacting.

9. A process for preparing a crop protection solid active compound formulation as claimed in claim 1, which comprises dissolving a cyclohexenone oxime ether of the general formula I in an organic solvent, extracting with an aqueous solution of the water-soluble basic salt and then removing the water.

10. A process as claimed in claim 9, wherein the crop protection solid active compound formulation is optionally comminuted after removing the water and then agglomerated or compacted.

11. A process as claimed in claim 8, wherein extruder granulation, disk granulation, fluidized bed granulation or mixer granulation is used for agglomeration.

12. A process for controlling undesired vegetation, which comprises dissolving a herbicidally active amount of a crop protection solid active compound formulation as claimed in claim 1 and applying the active compound to the crop plant, its habitat and/or on its seed.

13. A stable, water-soluble crop protecion solid active compound formulation as defined in claim 1, comprising, as crop protection active compound, a cyclohexenone oxime ether I wherein $R^2$ is sodium, $R^3$ is tetrahydrothiopyran-3-yl, $R^4$ and $R^5$ are hydrogen, Alk is $CH_2CH(CH_3)$ and $R^6$ is p-fluorophenoxy or p-chlorophenoxy.

14. A crop protection solid active compound formulation as defined in claim 6, comprising glyphosate or a salt thereof as further crop protection active compound.

15. A crop protection solid active compound formulation as defined in claim 7, comprising glyphosate or a salt thereof as further crop protection active compound.

16. A compound as in claim 13, which is the sodium salt of 2-[1-(2-p-chlorophenoxypropyloxy)iminobutyl]-5-(tetrahydrothiopyran-3-yl)-3-hydroxycyclohexenone.

* * * * *